United States Patent [19]
Frohardt et al.

[11] Patent Number: 4,830,504
[45] Date of Patent: May 16, 1989

[54] GLOSS GAUGE

[75] Inventors: Allen Frohardt, San Jose; John A. Dahlquist, Palo Alto; John J. Howarth, Monte Sereno, all of Calif.

[73] Assignee: Measurex Corporation, Cupertino, Calif.

[21] Appl. No.: 65,942

[22] Filed: Jun. 24, 1987

[51] Int. Cl.$^4$ .......................... G01N 21/55; G01J 1/18
[52] U.S. Cl. ...................................... 356/448; 356/243
[58] Field of Search ................. 356/448, 243; 350/584

[56] References Cited

U.S. PATENT DOCUMENTS

| | | | |
|---|---|---|---|
| 2,739,246 | 3/1956 | Hunter | 356/448 |
| 3,591,291 | 7/1971 | Greer et al. | 356/448 |
| 3,607,623 | 9/1971 | Chappelle | 356/448 |
| 3,890,049 | 6/1975 | Collins et al. | 350/584 |
| 3,960,077 | 6/1976 | Aylett | 356/448 |
| 4,240,691 | 12/1980 | Holmqvist et al. | 350/584 |

*Primary Examiner*—Richard A. Rosenberger
*Attorney, Agent, or Firm*—Spensley Horn Jubas & Lubitz

[57] ABSTRACT

A device for determining gloss on a surface having a calibrating feature wherein a gloss calibration standard is provided by means of a built-in standardization surface. The standardization surface provides a reference to which the gloss of a sample surface is compared. The standardization surface is protected from dust build-up throughout the operation of the device.

9 Claims, 3 Drawing Sheets

GLOSS GAUGE

BACKGROUND OF THE INVENTION

The present invention relates to a device for optically measuring the gloss of a surface, and more particularly, to a gloss gauge which is calibrated with reference to the reflectance of a surface having of a known gloss.

One of the parameters used in determining the quality of a particular surface is the surface luster or the gloss of the surface. For example, in paper production, various grades of paper having different surface gloss are produced to suit various applications. During paper production, it is desirable to periodically or continuously measure the gloss of the surface of the paper to ensure that the paper surface has the desired gloss.

Typically, the surface gloss of paper is measured using a gloss gauge during the last step of paper production before the finished paper, which is manufactured in a continuous sheet, is packaged in the form of rolls. The rolls of paper are then shipped to paper products manufacturers who process the paper sheet in accordance with the intended use.

Certain devices for determining the gloss of paper surfaces comprise an optical system which measures the intensity of a beam of light reflected from the paper surface. Typically, the gloss of the paper surface is determined by comparing its reflectance to the reflectance of a known gloss standard, such as, for example, a glass tile having a polished surface with a known gloss. Specifically, in measuring the reflectance of the paper surface, light is projected onto the surface, and a sensor which is responsive to the intensity of light is positioned to measure the intensity of the light reflected from the paper surface. The gloss gauge measures the reflectance of the tile surface in the same manner by substituting the tile surface for the paper surface. The reflectance of the paper surface is referenced to the reflectance of the tile surface, thereby providing a measure of the gloss of the paper surface. In practice, the reflectance measurement of the tile surface is periodically performed, off-sheet and between scans, as the gloss gauge scans back and forth across the paper surface. The gloss gauge is calibrated during each such measurement with the known reflectance of the tile surface.

Certain gloss gauges require relatively complex mechanisms for maneuvering the standardization tile into position for a reflectance measurement and then moving the tile out of the way of the light beam for reflectance measurements of the paper surface. Moreover, because of their complexity, it is difficult for such mechanisms to maintain a proper constant angular alignment of the tile with respect to the optical system of the gloss gauge. Such alignment is critical to proper reflectance measurements since reflectance is very sensitive to changes in angular alignment of the reflecting surface.

Also, the tile surface used in certain gloss gauges is subject to dust build-up. Dust particles, generated by the paper mill during the paper production process, may cover the tile surface. The dust particles alter the reflectance of the tile surface. As a result, a gloss gauge having a dust-contaminated tile surface will not provide a true comparison of the reflectance of the tile surface to the paper surface. Frequent cleaning of the tile surface has therefore been required to maintain an acceptable gloss standard.

SUMMARY OF THE INVENTION

The present invention is directed toward a device called a gloss gauge which is used for measuring the gloss of a surface (hereinafter a "sample surface") by directing a beam of light at a sample surface and electronically comparing the reflectance of the sample surface to that of a built-in reference or standardization surface having a known gloss. The sample surface may be, for example, the surface of a sheet of paper as it emerges from the calender rolls of a paper making machine. The standardization surface may be the surface of a polished glass tile.

In the device of the present invent the standardization surface is protected from dust build-up throughout the operation of the device. The present device also makes use of a mechanism which is less mechanically complex and more accurate than those previously known to position the standardization surface in the path of the light beam during calibration of the gloss gauge.

To accomplish the above, the positioning mechanism of the present invention comprises a cylinder assembly which encloses the standardization surface. More specifically, the standardization surface is attached to a piston which is slidable in the cylinder assembly. The cylinder assembly is mounted inside a casing which encloses an optical system including a light beam source and a light intensity sensor. In operation, when measuring the gloss of a surface, the piston is retracted to a first position so that the standardization surface is positioned above the surface whose gloss is to be measured and out of the path of the light beam. When the reflectance of the standardization surface is to be measured, the standardization surface can be lowered by the piston to a second position in the same plane as the sample surface.

The reflectance of the sample surface is determined by directing a light beam from the light source within the casing at an angle at the sample surface and measuring the intensity of the light specularly reflected from the surface. When reflectance of the standardization surface is to be measured, the entire gloss gauge is moved off the sample surface and the piston is lowered to its second position so that the standardization surface is in the path of the incident light beam. The reflectance of the standardization surface is then determined in the same manner as was the reflectance of the sample surface. The gloss of the sample surface is determined by comparing the measured intensity of the light reflected from the sample surface with the measured intensity of the beam when it is reflected by the standardization surface.

Throughout the above operations, the standardization surface is enclosed in the piston assembly to protect it against dust build-up on its surface which would otherwise alter the reference reflectance. The optical components of the present gloss gauge are also protected against dust contamination by the casing in which they are enclosed.

Openings are provided in the piston itself and in the surrounding cylinder assembly to pass incident light from the light source to the sample surface or standardization surface and to pass reflected light from the sample surface or standardization surface to the light sensor. The openings in the cylinder assembly are covered with windows to prevent dust from entering the optical system enclosed in the gloss gauge casing. To ensure that there is no dust build-up on these windows which would alter the intensity of the incident light beam, air outlets are provided adjacent to the windows to direct a stream of filtered air away from the windows. These air streams blow dust off of the windows and, since the air streams are directed away from the windows, prevent dust particles from approaching the windows. Moreover, the air streams may also clear the sample surface of any dust particles which would otherwise alter the reflectance of the surface.

To account for changes in the intensity of the light source, during the continuous or periodic gloss measurements of a number of sample surfaces or several portions of the same sample, a portion of the light beam from the light beam source is directed to a reference light sensor. This sensor monitors the intensity of the light beam emitted by the light source. Changes in the intensity of the beam emitted by the light beam source alters the intensity of the light directed at the sample surface and hence affects the reflectance measurement. According to the present invention, the reflectance measured by the light intensity sensor is compensated in accordance with the changes in light source intensity detected by the reference sensor.

DETAILED DESCRIPTION OF THE PREFERRED EMBODIMENT

The following description is of the best presently contemplated mode of carrying out the invention. In the accompanying drawings, like numerals designate like parts in the several figures. This description is made for the purpose of illustrating the general principles of the invention and should not be taken in a limiting sense. The scope of the invention is best determined by reference to the accompanying claims.

Figure 1:
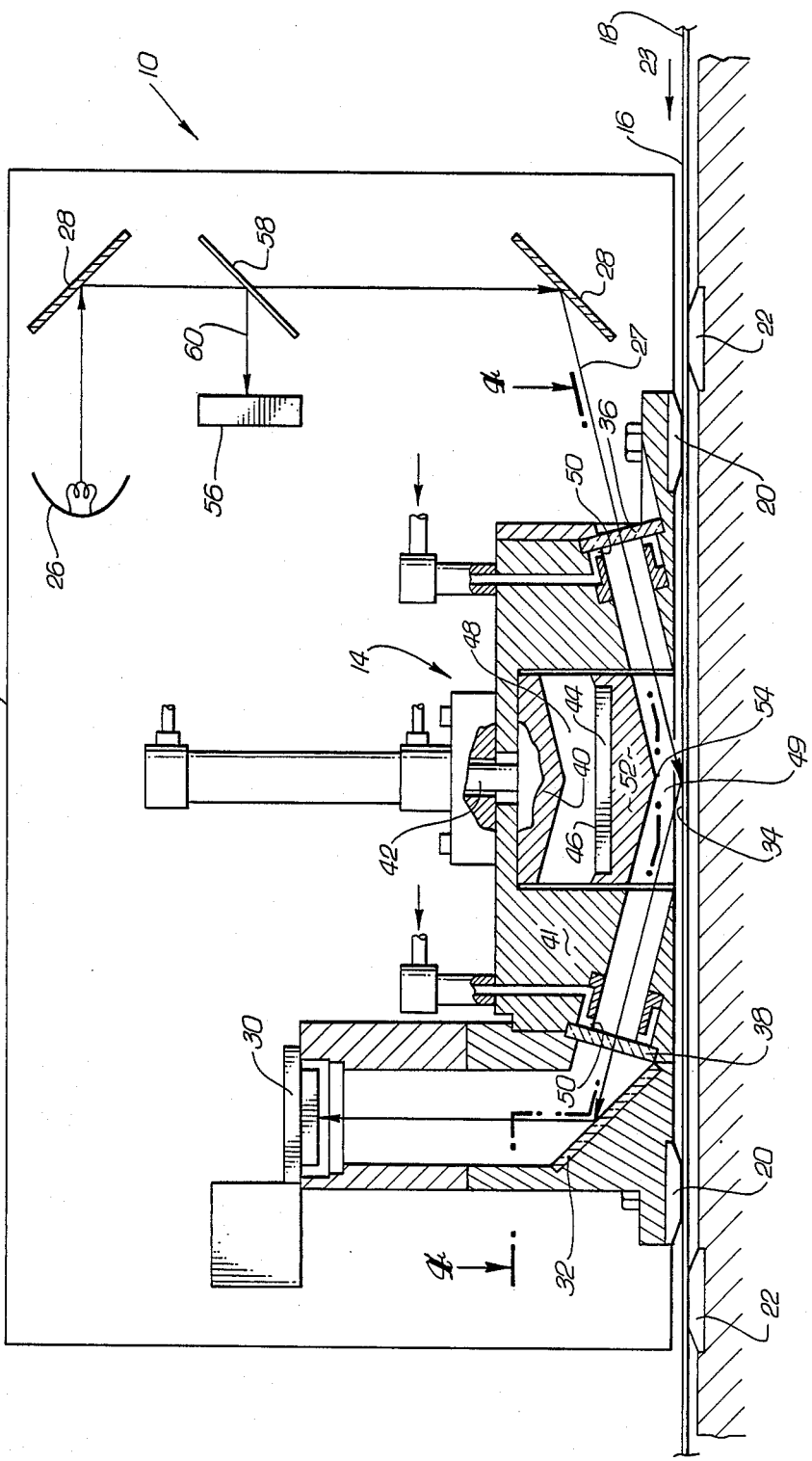
FIG. 1 is a schematic cross-sectional view of the present invention illustrating the position of the standardization tile while the reflectance of the paper surface is being measured.
Figure 2:
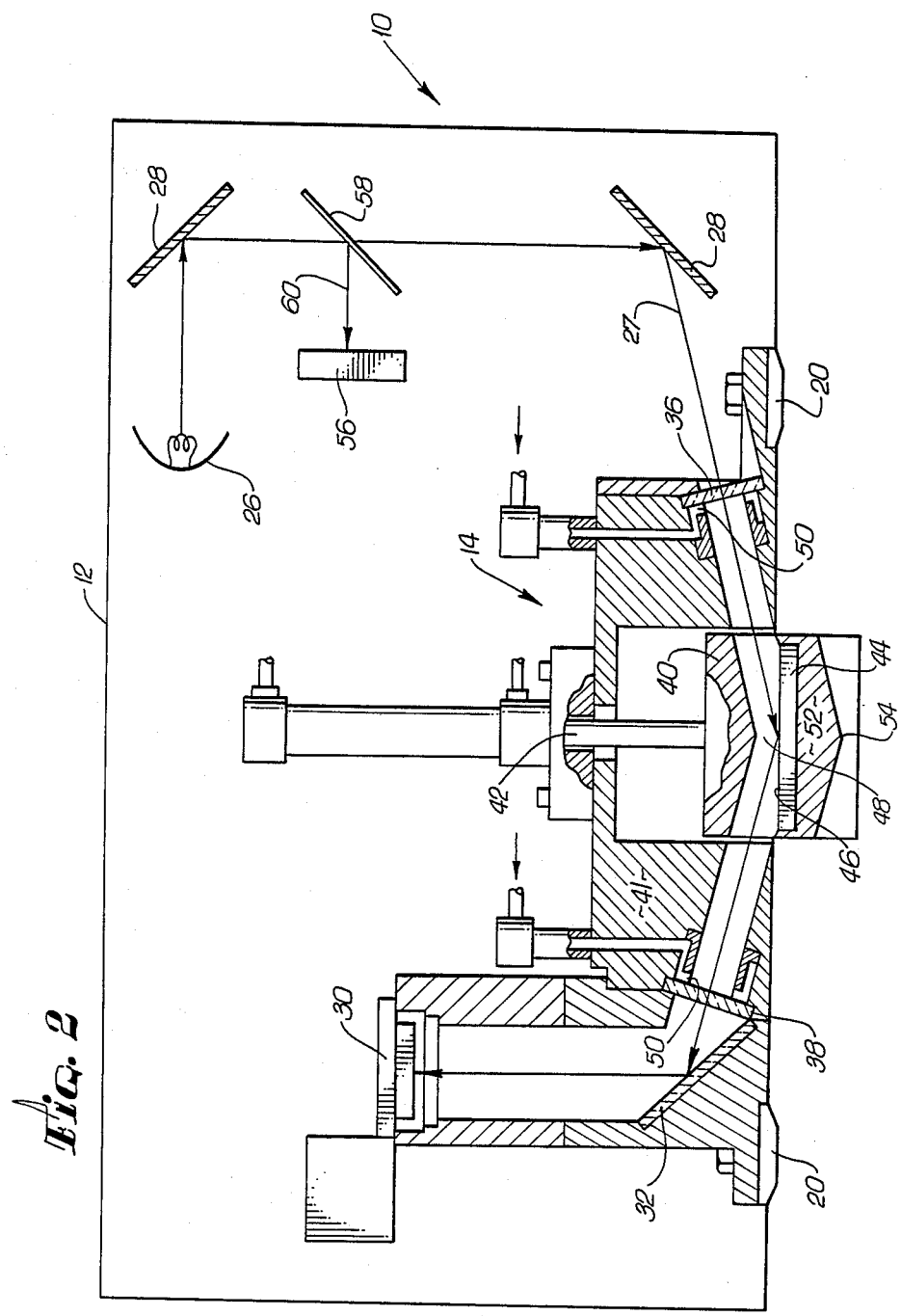
FIG. 2 is a schematic cross-sectional view of the present invention illustrating the position of the standardization tile while its reflectance is being measured.

A gloss gauge 10 according to the present invention is shown in FIGS. 1 and 2. The body of the gloss gauge is made up of a casing 12 and a cylinder assembly 14 together forming an enclosure containing the optical components of the device which will be described later. The gloss gauge 10 is placed adjacent a surface such as one side 16 of a sheet of paper 18 whose gloss is to be measured. The gloss gauge 10 of the present invention may be used to measure the gloss of the surface of any material. However, for convenience, the present invention will be described hereinafter specifically with reference to measuring the gloss of a sheet of paper 18.

Paper guides 20 are provided to maintain a predetermined spacing between the paper surface 16 and the adjacent side of the gloss gauge 10. Additionally, paper guides 22 are provided on the opposite side of the sheet of paper 18. The paper guides 22, in conjunction with the paper guides 20, maintain the sheet of paper 18 in a taut condition as the paper sheet 18 moves under the gloss gauge 10 in the direction of the arrow 23.

As illustrated in FIG. 1, the reflectance of the paper surface is being measured. Within the casing 12 a light source 26 is provided which projects a beam of light 27 onto the paper 18 using mirrors 28. The light beam 27 illuminates a portion 34 of the paper surface 16. The incident light 27 reflects off the paper surface 34 and is directed by a mirror 32, to a light intensity sensor 30, such as a photodiode. The light intensity sensor 30 measures the intensity of the light reflected from the surface 34.

Figure 4:
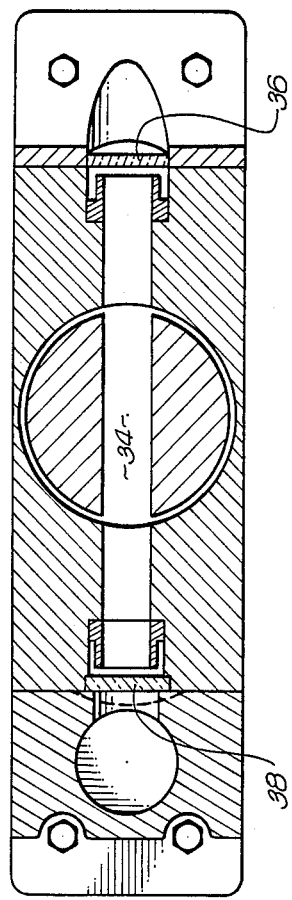
FIG. 4 is a top view of the cylinder assembly as seen from the inside of the cylinder assembly along line 4—4 in FIG. 1.

The optical components of the gloss gauge 10 are completely enclosed in the space defined by the casing 12 and the cylinder assembly 14 and thus protected from dust build-up. The cylinder assembly 14 is mounted inside the casing 12 and is centered above the paper surface 34 as shown in FIGS. 1 and 4. Within the cylinder assembly 14, a piston 40 is slideably fitted inside a cylinder 41 and is connected to an air actuated piston rod 42 for moving the piston 40 up and down inside the cylinder 41. A glass tile 44 having a surface 46 of a known standard gloss, i.e. the standardization surface, is positioned inside the piston 40. Windows 36 and 38 are provided on each side of the cylinder 41 to allow transmission of incident light and reflected light, respectively, through the cylinder 41 to and from the paper surface 34. The windows prevent dust from entering the casing 12 and settling on the optical components.

When refection of the paper surface is being measured, the tile surface 44 is raised by retracting the piston rod 42. In this position (FIG. 1), the tile surface 46 is not exposed to light from the light source 6. Furthermore, the tile surface is enclosed by the cylinder 41. The tile surface 46 is thus protected from dust particles which may be present in the surrounding environment.

Referring to FIG. 2, when reflectance of the tile surface is to be measured, the gloss gauge 10 is moved off the edge of the sheet of paper 18 and the tile 44 is lowered by extending the piston rod 42. In this position, light 27 from the light source 26 is incident on the tile surface 46 and the reflectance of this surface 46 is measured by the light intensity sensor 30. When the piston rod is lowered, the tile surface 46 is in a same plane, in relation to the light source 26 and the light intensity sensor 30, as the paper surface 34 when its reflectance is being measured. In other words, the alignment of the tile surface 46 relative to the light beam 27 is the same as the alignment of the beam 27 to the paper surface 34 when its reflectance is being measured. It is important to maintain the same alignment for the two reflectance measurements since the amount of light which a surface reflects is very sensitive to the angle and position at which the incident light strikes the surfaces. In practice, following the paper industry standard for gloss measurements, it is usually preferred that the incident light beam be maintained precisely at an angle of 15° to the reflecting surfaces and that the intensity of the reflected light be measured precisely at this same angle.

The piston 40, in conjunction with the cylinder 41, protects the tile surface 46 from dust and dirt in the environment both when the reflectance of the tile surface 46 is being measured and when the reflectance of the paper sheet 18 is being measured. As a result, the tile surface 46 is kept clean throughout the operation of the gloss gauge. The reflectance of the tile surface therefore remains constant, thereby improving the accuracy of gloss measurement.

In practice, the reflectance of the standard tile surface is measured first, followed by a number of reflectance measurements of the paper surface. The previously measured reflectance value of the tile surface is compared to each subsequent reflectance measurement of the paper surface until the gloss gauge is recalibrated by the next tile reflectance measurement. Typically, the gloss gauge is scanned back and forth across the paper sheet to measure the gloss of the surface in the cross direction, i.e. across the width of the paper, as the paper is coming off a system of calender rolls in the paper mill in a direction perpendicular to the scan direction. It is only necessary to periodically measure the reflectance of the standard tile surface to update the tile reflectance value after a predetermined number of scans back and forth across the sheet. The gloss sensor can, but need not, be calibrated after every journey across the sheet.

Figure 3:
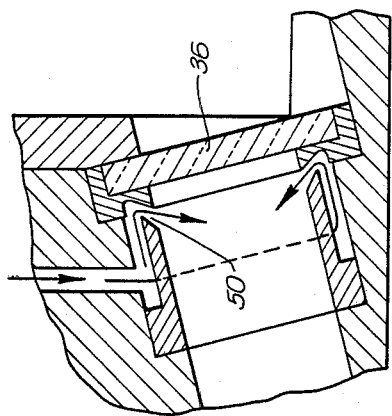
FIG. 3 is an enlarged view of the window region of the cylinder assembly illustrating the annular air outlet.

To further improve the accuracy of the gloss gauge of the present invention, the windows 36 and 38 are protected from dust accumulation which may affect the intensity of the incident light beam 27 or the light reflected to the light intensity sensor 30 during a gloss measurement. The windows 36 and 38 are set back in the cylinder 41 from the piston 40 along channel 48 and the windows 36 and 38 are kept clear by means of introducing streams of filtered air into the channel 48 from holes adjacent to the windows 36 and 38. Preferably, the air is introduced through an annular opening 50 around each window, as shown in FIG. 3. The flow of filtered air will prevent dust particles from approaching the windows. The air so introduced can also lift any dust particles that may have collected on the windows. Consequently, there is little or no dust contamination on the windows to affect the intensity of the incident light or the reflected light. One way of providing air at the windows is to pressurize the interior of the casing 12 with filtered air and allow this air to escape from the openings 50 around the windows 36 and 38.

As shown in FIGS. 1 and 2, channel 48 in the piston 40 may be in a V-shaped configuration formed by two holes bored from the sides of the piston 40 at an angle to one another. The channel 48 is in alignment with the windows 36 and 38 at the extended position of the piston rod 42 (FIG. 2), thereby exposing the tile surface 46 to incident light from the light source 26 and allowing reflected light from the tile surface 46 to pass through the channel to the light intensity sensor 30.

The lower portion 52 of piston 40 also has a V-shape channel 49, as shown in FIGS. 1-2. This V-shaped channel 49 is in alignment with the windows at the retracted position of the piston rod 42 when the reflectance of the paper surface is being measured, as shown in FIG. 1. The V-shape of the channel 49 smooths out the flow of the air streams and thereby prevents dust from being circulated by air currents within the channel 49 and deposited on the windows 36 and 38. Specifically, if the portion 52 of the piston 40 below the tile 44 were flat, rather than V-shaped, the air streams coming from the holes 50 adjacent to the windows may create a recirculating flow of air within the space defined between the paper sheet 18 and the lower part 52 of the piston 40 rather than flowing smoothly out between the gloss gauge 10 and the sheet 18. Any dust that may have been carried within the recirculating flow will be set in motion in the space between the piston 40 and sheet 18 and consequently the light passage within this space may be clouded, thereby affecting the intensity of light through the passage. Also, this dust may settle on windows 36 and 38. However, the V-shaped channel 49 promotes a smooth air flow from the filtered air outlets 50, through channel 49 and out through the space between the gloss gauge casing 12 and the sheet surface 16, thereby sweeping dust out of channel 49 rather than merely stirring it up inside the channel 49.

To further improve the accuracy of gloss measurement by the gloss gauge 10, the present invention compensates for variations in the intensity of the light source 26. Light intensity may change due to several factors including a change in the power supplied to the light source 26, deterioration of the light source 26, and dust build up on the light source 26. If the intensity of the light source 26 changes between gloss standardization measurements using the tile 16 surface described above, the reflectance of the paper surface as measured by the light intensity sensor 30 will change accordingly, even though there is no actual variation in the reflectance of the paper surface 16. Thus, if the changing condition of the light source 26 were not accounted for, the measured reflectance would not be a true indication of the gloss of the paper surface 16.

To overcome this problem, the condition of the light source 26 is constantly monitored by measuring the intensity of light from the light source 26 by means of a reference sensor 56. A beam splitter 58 is placed in the light path between the light source 26 and the paper surface 34 to direct a portion of the light to the reference sensor 56. The reference sensor 56 measures the intensity of a portion of the light beam 60 which is split from the main light path 27. Based on the changes in the intensity of the beam 60, the changes in the light intensity of the main light beam 27 may be determined. The intensity of the light reflected from the paper surface 34 as measured by the reflectance sensor 30 can then be compensated for in accordance with the detected change in incident light intensity.

In summary, the present invention provides an apparatus for measuring gloss on a surface having means of calibration in reference to a standard gloss surface which is protected from dust accumulation. The reference gloss measurement is accomplished requiring only simple movement of the standardization tile in a direction normal to the sample surface, thereby enabling the standardization surface to be maintained in an accurately predetermined relationship to the optical components of the gloss gauge. Means for compensating for changes in the condition of the light source is also provided. Moreover, air streams are directed in a manner to further prevent dust build-up on the optical surfaces of the gloss gauge and to blow dust off the sample surface.

One preferred embodiment of the present invention has been described. Nevertheless, it will be understood that various modifications may be made without departing from the spirit and scope of the invention. Furthermore, although the present invention has been described with reference to the gloss measurement of paper, the present invention is also suitable for measuring the gloss of surfaces other than of paper. Accordingly, it is to be understood that the invention is not to be limited by the specific illustrated embodiment, but only by the scope of the appended claims.

We claim:

1. A gloss gauge for optically measuring the gloss of a sample surface when said surface is disposed in a gloss measuring plane, comprising:
   a light beam source;
   means for directing an incident light beam from the light beam source to the gloss measuring plane;

reflectance sensing means for sensing the intensity of the light beam reflected from the gloss measuring plane;

a standardization member having a standardization surface on one side thereof, the standardization surface having a known gloss;

an enclosure for excluding reflectance-altering material from the standardization surface, said enclosure including a first transparent member disposed in a wall of the enclosure to transmit the incident light beam from the light beam source to the gloss measuring plane and a second transparent member disposed in a wall of the enclosure to transmit reflected light from the gloss measuring plane to the reflectance sensing means; and an actuator for moving the standardization surface with respect to the enclosure, while maintaining the standardization surface within the enclosure, from a first position which is out of the gloss measuring plane to a second position which is in the gloss measuring plane.

2. A gloss gauge as in claim 1, wherein the actuator moves the standardization surface, with respect to the enclosure, linearly from the first to the second position and from the second to the first position.

3. A gloss gauge as in claim 2, wherein the incident light beam is directed at the standardization surface at the same angle of incidence as the incident light beam is directed at the sample surface, when a sample surface is disposed in the gloss measuring plane, and the light beam reflected from the standardization surface is sensed by the reflectance sensing means at the same angle of reflection as the light beam reflected from the sample surface, when a sample surface is disposed in the gloss measuring plane.

4. A gloss gauge as in claim 1, further comprising means for directing jets of dust-free fluid toward the gloss measuring plane and away from the first and second transparent members.

5. A gloss gauge as in claim 4, wherein the means for directing jets of dust-free fluid includes a fluid jet opening encircling each of the first and second transparent members.

6. A gloss gauge as in claim 4, wherein the actuator includes a piston slidably mounted within the enclosure, the piston defining a channel therein through which the incident and the reflected light beams can travel, said channel leading from the first and second transparent members toward the standardization surface, when the standardization surface is in the second position.

7. A gloss gauge as in claim 6, wherein the enclosure defines first and second channels for guiding the jets of dust-free fluid away from the transparent members and toward the gloss measuring plane, and wherein a portion of the piston is disposed adjacent to the standardization member on the side of the member opposite the standardization surface, said portion having a V-shape pointing away from the standardization member such that, when the standardization member is in the first position, the V-shaped position forms a substantially continuous extension of the walls of the first and second channels to thereby suppress turbulent air flow within the space between the surface of the v-shaped piston portion and the gloss measuring plane.

8. A gloss gauge as in claim 1, further comprising:

reference intensity sensing means for sensing the intensity of the light beam emitted from the light beam source;

means for directing a portion of the incident light beam from the light beam source to the reference intensity sensing means before the incident light beam reaches the gloss measuring plane; and means for compensating for the intensity of light sensed by the reflectance sensing means in accordance with the intensity of light sensed by the reference intensity sensing means.

9. A gloss gauge as in claim 1, further comprising:

reference intensity sensing means for sensing the intensity of light from the light source;

means for directing a portion of the light from the light source to the reference intensity sensing means before the light reaches the sample surface or the standardization surface; and means for compensating for the intensity of light measured by the reflectance sensing means in accordance with the intensity of light measured by the reference intensity sensing means.

* * * * *